(12) United States Patent
Mahmoudi et al.

(10) Patent No.: US 9,161,996 B2
(45) Date of Patent: Oct. 20, 2015

(54) GOLD COATED SUPER PARAMAGNETIC IRON OXIDE NANO-PARTICLES (SPIONS) AND A METHOD OF SYNTHESIZING THE SAME

(76) Inventors: Morteza Mahmoudi, Tehran (IR); Mohammad Ali Shokrgozar, Tehran (IR)

( * ) Notice: Subject to any disclaimer, the term of this patent is extended or adjusted under 35 U.S.C. 154(b) by 548 days.

(21) Appl. No.: 13/098,417

(22) Filed: Apr. 30, 2011

(65) Prior Publication Data
US 2011/0206619 A1 Aug. 25, 2011

Related U.S. Application Data

(60) Provisional application No. 61/447,740, filed on Mar. 1, 2011.

(51) Int. Cl.
| | | |
|---|---|---|
| *A61K 49/18* | (2006.01) | |
| *A61K 47/48* | (2006.01) | |
| *A61K 49/00* | (2006.01) | |
| *B82Y 5/00* | (2011.01) | |
| *B82Y 25/00* | (2011.01) | |
| *G01N 21/65* | (2006.01) | |
| *H01F 1/00* | (2006.01) | |
| *C23C 18/16* | (2006.01) | |
| *G01R 33/56* | (2006.01) | |

(52) U.S. Cl.
CPC ........... *A61K 49/1857* (2013.01); *A61K 47/489* (2013.01); *A61K 49/00* (2013.01); *A61K 49/0002* (2013.01); *A61K 49/0065* (2013.01); *A61K 49/0093* (2013.01); *A61K 49/183* (2013.01); *A61K 49/186* (2013.01); *A61K 49/1827* (2013.01); *A61K 49/1851* (2013.01); *A61K 49/1872* (2013.01); *B82Y 5/00* (2013.01); *B82Y 25/00* (2013.01); *G01N 21/658* (2013.01); *H01F 1/0054* (2013.01); *C23C 18/1646* (2013.01); *G01R 33/5601* (2013.01)

(58) Field of Classification Search
CPC ............ A61K 49/183; A61K 49/1851; A61K 18/1646; A61K 47/489; A61K 49/0065; A61K 49/00; G01N 21/658
See application file for complete search history.

(56) References Cited

PUBLICATIONS

Jin, Y., et al., "Multifunctional nanoparticles as coupled contrast agents", 2010, Nature Communications, pp. 1-8.*
Kunz, M.S., et al., "Morphologies of discontinuous gold film on amorphous polymer substrates", 1992, J. Applied Physics, pp. 4458-4460.*
Malynych, S., et al., "Polyvinyl pyridine) as a Universal Surface Modifier for Immobilization of Nanoparticles", 2002, J. Phys. Chem., 106, pp. 1280-1285.*
Wang, H., et al., Plasmonic Nanostructures: Artificial Molecules, 2007, Acc. Chem. Res., 40, pp. 53-62.*
Zhai, Y., et al., "Fabrication of Iron Oxide Core/Gold Shell Submicrometer Spheres with Nanoscale Surface Roughness for Efficient Surface-Enhanced Raman Scattering", 2009, J. Phys. Chem C., 113, pp. 7009-7014.*
Gupta, A.K., et al., "Synthesis and surface engineering of iron oxide nanoparticles for biomedical applications", 2005, Biomaterials, pp. 3995-4021.*

* cited by examiner

Primary Examiner — Michael G Hartley
Assistant Examiner — Lance Rider
(74) Attorney, Agent, or Firm — Barry Choobin; Patent 360

(57) ABSTRACT

The various embodiments herein provide a gold coated SPIONs with jagged surface. The gold coated SPIONs have a core and a shell. The core is a SPION molecule and the shell is a jagged gold layer. A non-uniform polymeric gap exists between the core and the shell. The embodiments also provide a method of producing the jagged gold coated SPIONs by mixing a colloidal dispersion of SPIONs with pH sensitive polymers. Adding a gold salt to the above mixture and reducing the gold salt to form jagged gold coated SPIONs.

14 Claims, 16 Drawing Sheets

GOLD COATED SUPER PARAMAGNETIC IRON OXIDE NANO-PARTICLES (SPIONS) AND A METHOD OF SYNTHESIZING THE SAME

CROSS-REFERENCE TO RELATED APPLICATIONS

This application claims the benefit of U.S. provisional patent application Ser. No. 61/447,740, filed Mar. 1, 2011, which is incorporated herein by reference in its entirety.

BACKGROUND

1. Technical Field

The embodiments herein generally relate to the field of molecular imaging and particularly to multimodal molecular imaging. The embodiments herein more particularly relate to gold coated super paramagnetic iron oxide nano-particles. The embodiments herein also relate to a method of synthesizing the gold coated super paramagnetic iron oxide nano-particles with a jagged surface.

2. Description of the Related Art

With the entry of nanoscience in the medical field, one can hope for early diagnosis together with the prompt treatment of catastrophic diseases like (e.g. cancer). The treatment of these catastrophic diseases has been dramatically increased with the entrance of nanoscience. Development of multifunctional engineered nanoparticles (NPs) with desired physiochemical properties, as nano-probes, has enabled new imaging modalities which have great capability in molecular imaging and medical theragnosis and which are essential for early detection and rapid treatment of diseases. It is noteworthy to mention that these multimodalities of engineered NPs are beyond the observed intrinsic properties of individual NPs comprising materials. In the recent few decades, nanoparticles (NPs) have been recognized as promising candidates for the creation of new revolution in science and technology due to their unusual properties which have attracted the attention of physicists, chemists, biologists and engineers. The appearance of NPs in medical sciences either introduced new opportunities or caused significant enhancements in the conventional biomedical methods (e.g. imaging purposes). The creation of novel engineered multimodal NPs is a key focus in bio-nanotechnology and can lead to advancement in the deep understanding of the biological processes at the biomolecular level thereby causing the great impact on molecular diagnostics, imaging and therapeutic applications.

Ever since the medical diagnosis era was initiated by Wilhelm Roentgen, who captured the first X-ray image of his wife's hand in 1896, X-rays have been extensively employed in the medical imaging of anatomical details. However, cellular and molecular imaging still remained as dreams in medical field. With the development of nano science, this dream is coming true. The advantage of using multimodal NPs, in comparison with individual NPs (e.g. semiconductor quantum dots, magnetic and metallic NPs), for cellular or biomolecular tracking, is the capability of multimodal NPs to provide a high spatial resolution with high anatomic background contrast, together with the lack of exposure to ionizing radiation and the ability to follow the cells for months.

During the last decade, various approaches using different imaging techniques as well as various contrast agents have been employed to enhance the efficacy of biomolecular imaging. Among the various NPs employed in the biomolecular imaging methods, the super paramagnetic iron oxide nano particles (SPIONs) have been recognized as one of the most important nano-probes because of their multi-modality and multi-tasking property. Various methods have been employed for producing these SPIONs. One of the methods involves employing a polyol route. Briefly, 5 mL of an aqueous solution of $FeCl_2.4H_2O$ (0.045 mol) and $FeCl_3$ (0.0375 mol) were added to 250 mL of diethylene glycol. The mixture was heated to 170° C. and maintained at this temperature for 15 min before addition of the base (i.e. solid NaOH (0.375 mol)). Afterward, the temperature was maintained at 170° C. for a period of 1 h before cooling at 60° C. The synthesized SPIONs were collected with neodymium magnet and washed with 100 mL of a $HNO_3$ 1N solution. The SPIONs have excellent biocompatibility.

Individual NPs, as nanoprobes, present their distinct advantages and limitations. In this case, super paramagnetic iron oxide NPs (SPIONs) are recognized as suitable contrast agent in T2-weighted magnetic resonance imaging (MRI). However, SPIONs are not sensitive in optical imaging or positron emission tomography. In order to make them sensible to other imaging modes (e.g. optical imaging), their surfaces or structures should be modified. For examples, radioactive-doped SPIONs could be traced with positron emission tomography and gamma spectroscopy imaging methods.

Gold NPs with their unique optical and melting properties were introduced in 1996 by an aggregation of gold NPs (at a diameter of 13 nm) and oligonucleotides. The above mentioned aggregate scattering properties together with the interaction between particle surface plasmons as the distance between NPs resulted in a variation in the color of gold NPs. This distance-dependent optical property has led to the use of gold NPs in a plethora of biomolecular detection methods, starting with colorimetric systems. More specifically, the gold NP bioconjugates were employed for the detection of polynucleotide using the change in optical properties resulting from plasmon-plasmon interactions between locally adjacent gold NPs. Due to their colorimetric contrast which is induced by surface plasmon resonance, the gold NPs can be used as contrast agents in biomolecular imaging. The main problem with individual gold NPs for in vivo imaging applications is their low tissue penetration depth which is limited to millimeters. Therefore, a major challenge is how to engineer or enhance molecular probes with integrated functionalities while still maintaining the compact sizes. In addition, it is highly attractive to have multi-task-nano probes with several functionalities which enable new imaging modes, not available from each individual component for enhanced contrast specificity. Several reports disclose the works on the creation of multimodal coupled NPs to achieve better molecular imaging, for instance Loo et al. employed a novel class of contrast agents based on nanoshell (i.e. composition of a dielectric silica core covered by a thin gold shell) bioconjugates for biomolecular imaging. The authors claimed that nanoshells have a great potential to offer advantages over conventional imaging probes, such as continuous and broad wavelength tunability, far greater scattering and absorption coefficients, increased chemical stability, and improved biocompatibility. According to their results, the prepared nanoshell bioconjugates could be used for targeting and imaging of human epidermal growth factor receptor 2 (i.e. HER2) in live human breast carcinoma cells. The same group employed these nanoshells for dual imaging or therapy to detect and destroy breast carcinoma cells that over-express HER2. It has been shown that gold high-density lipoprotein NPs, as contrast agents, can significantly improve CT imaging for characterization of macrophage burden, calcification, and stenosis of atherosclerotic plaques.

The combination of gold and magnetic NPs (i.e. gold coating on the surface of magnetic NPs) with controllable shell thickness and smooth surface can be used for multi-task applications including contrast enhancing in MRI, magnetic attraction, near-infrared absorption (NIR), and photon scattering applications. Lyon et al. reported a formation of stable magnetic core-shell NPs in aqueous media through rapid and effective route. The several reports are dedicated to the creation of direct gold coating on the surface of SPIONs. None of the approach simultaneously produces NPs with NIR response and also the obtained materials are critical for in vivo imaging and therapy, and maintains compact particle size, which affects tissue penetration and plasma circulation. Jin et al. reported a new generation of compact, uniform, NIR responsive gold coated SPIONs by creating a gap between the core and the shell. The smooth gold-shell SPIONs were prepared according to the previous report. Briefly, the prepared SPIONs were mixed with PL-PEG-COOH (ratio of 1:1.5 W/W) in chloroform and remained, till the solvent were evaporated slowly. The residual coated SPIONs were heated to 80° C. for 5 min and re-dispersed in DI water with sonication. The obtained materials were collected with strong magnet and washed several times with DI water. PLH was added to the solution of SPIONs and the pH was adjusted among 5-6, using 0.1 N HCl. After incubation for 60 min, the magnetic NPs were collected with magnet and washed several times with DI water. The obtained solution was mixed with $HAuCl_4$ (w/w 1%), for 20 min where the pH was adjusted among 9-10 with NaOH. Afterward, $NH_2OH \cdot HCL$ was added to the solution and mixed well till the colour of colloidal suspension turned to dark blue. It is noteworthy that the observed colour was cleared in a few minutes. The achieved solution was washed several times, re-dispersed in DI water using sonicator, and kept between 2-8° C. In this case, a magnetically sensitive NP with strong NIR and MRI responses together with magnetomotive photoacoustic (mmPA) imaging capability were obtained. But the responses obtained were not of the desired expectations and also there was no effect on Surface Enhanced Raman Spectroscopy (SERS).

Hence there is a need to engineer a new generation of compact and uniform gold coated SPIONs by creating a non-uniform gap between the core and the shell with enhanced imaging properties and Surface Enhanced Raman Spectroscopic (SERS) properties.

The above mentioned shortcomings, disadvantages and problems are addressed herein and which will be understood by reading and studying the following specification.

OBJECTIVES OF THE INVENTION

The primary object of the embodiments herein is to provide a new gold coated super paramagnetic iron oxide nano-particle (SPIONS) with a polymeric gap and jagged surface.

Another object of the embodiments herein is to provide a gold coated SPIONS that are compact and uniform with a non-uniform gap between the core and the shell.

Yet another object of the embodiments herein is the use of pH stimuli-responsive polymers to generate a jagged surface for the gold coated spions.

Yet another object of the embodiments herein is to produce magnetically sensitive nanoparticles.

Yet another object of the embodiments herein is to provide a gold coated SPIONS acting as a nano-probe with profound impact on molecular diagnosis and cellular tracking, medical imaging and therapeutic applications like drug delivery or simultaneous imaging and drug delivery.

Yet another object of the embodiments herein is to provide a gold coated SPIONS as new imaging modal with surface enhanced Raman spectroscopy (SERS) that significantly enhances the capability of these nano-probes for molecular imaging purposes.

Yet another object of the embodiments herein is to provide a gold coated SPIONS that are multifunctional in nature with Near Infra Red spectroscopic (NIR), Magnetic Resonance Imaging (MRI) and Magneto motive photo acoustic imaging (mmPA) responses.

Yet another object of the embodiments herein is to provide a gold coated SPIONS that are a promising candidate in multimodal molecular imaging purpose.

Yet another object of the embodiments herein is to provide a multimodal imaging nano-probes with not only surface enhanced Raman spectroscopic properties but also electronic, magnetic, optical, acoustic and thermal response properties.

Yet another object of the embodiments herein is to provide gold coated spions with a jagged surface that conjugates with the bio-molecules in a simple manner through thiol binding and provides an all-in-one nano-probe for non-invasive imaging and molecular theranosis of complex diseases.

These and other objects and advantages of the embodiments herein will become readily apparent from the following detailed description taken in conjunction with the accompanying drawings.

SUMMARY

The various embodiments herein provide a multifunctional jagged gold coated magnetic nanoparticles, with a polymeric gap. The multifunctional jagged gold coated magnetic nanoparticles act as a powerful nanoprobe with profound impact on molecular diagnosis, imaging and therapeutic applications.

According to one embodiment herein, the gold coated super paramagnetic iron oxide nano-particle (SPION) comprises a core, a shell and a gap between the core and the shell. The core includes a super paramagnetic iron oxide nano-particle. The shell includes a jagged coating of gold. The gap is a polymeric gap. The core is made up of magnetite. The gap includes a plurality of polymeric molecules selected from a group comprising of poly(2-vinyl pyridine), PL-PEG-COOH and Poly-L-histidine. The poly(2-vinyl pyridine) is a pH sensitive polymer and has a folded shape. The PL-PEG-COOH is a Phospholipid-polyethylene glycol terminated with a carboxylic acid and has a stranded shape. The poly(2-vinyl pyridine) and Poly-L-histidine act as a template for the growth and nucleation of the jagged gold coating.

According to another embodiment herein, the gold coated SPION has various applications selected from a group comprising of Surface Enhanced Raman Spectroscopy (SERS), Magnetomotive Photoacoustic spectroscopy (mmPA) and Magnetic Resonance Imaging spectroscopy (MRI), Near Infra Red spectroscopy (NIR), drug delivery, drug delivery with simultaneous imaging, non-invasive imaging and molecular theragnosis and combination thereof.

According to one embodiment herein, a method of synthesizing gold coated super paramagnetic iron oxide nano-particle (SPION). In the method, a colloidal dispersion of SPIONS is prepared by a chemical method. A plurality of polymers is added. A gold salt is added. The added gold salt is then reduced and the gold coated super paramagnetic iron oxide nano-particle (SPION) is obtained. The gold coating is jagged in shape. The chemical method is selected from a group comprising of a co-precipitation method, a sol-gel method, a microemulsions method, a hydrothermal method, a thermal decomposition method, a polyol method, a sonochemical method and an electrochemical deposition method. The preferred methods are microemulsions method, a thermal decomposition method and a polyol method. The plurality of polymers include poly(2-vinyl pyridine), PL-PEG-COOH and Poly-L-histidine. The poly(2-vinyl pyridine) is a pH sensitive polymer. The pH sensitive polymer produces jagged gold coated SPIONS. The PL-PEG-COOH has a stranded shape. The PL-PEG-COOH is a Phospholipid-polyethylene glycol terminated with a carboxylic acid. The poly(2-vinyl pyridine) and Poly-L-histidine act as a template for a gold nucleation and growth. The gold salt herein is Chloroauric acid ($HAuCl_4$) in a concentration of 1%-2%. The gold salt is reduced by a Hydroxylamine Hydrochloride ($NH_2OH.HCl$) solution.

According to another embodiment herein, the method of producing gold coated super paramagnetic iron oxide nanoparticle (SPION) further comprises mixing a colloidal dispersion of SPIONS with Poly(2-vinylpyridine) and PL-PEG-COOH to form a mixture. Heating the mixture to 80° C. for 5 mins. Dispersing the heated mixture in DI water with sonication and adding PLH to the mixture to form a solution. Mixing the solution with a gold salt for 20 mins and adjusting a pH to 4-5 using a NaOH solution. Reducing the gold salt using $NH_2OH.HCl$ solution and obtaining the jagged gold coated SPIONS in a solution. Keeping the solution between 2-8° C. by re-dispersing in de-ionized water using a sonicator. The gold salt herein is $HAuCl_4$.

According to another embodiment herein, the ratio of SPIONS:Poly (2-vinylpyridine) used herein is 1:0.6-0.9 w/w. The ratio of SPIONS:PL-PEG-COOH used herein is 1:0.6-0.9 w/w. The ratio of SPIONS:PLH used herein is 1:1-2 w/w and the ratio of SPIONS:HAuCl4 used herein is 1:1-2%.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

Figure 1:
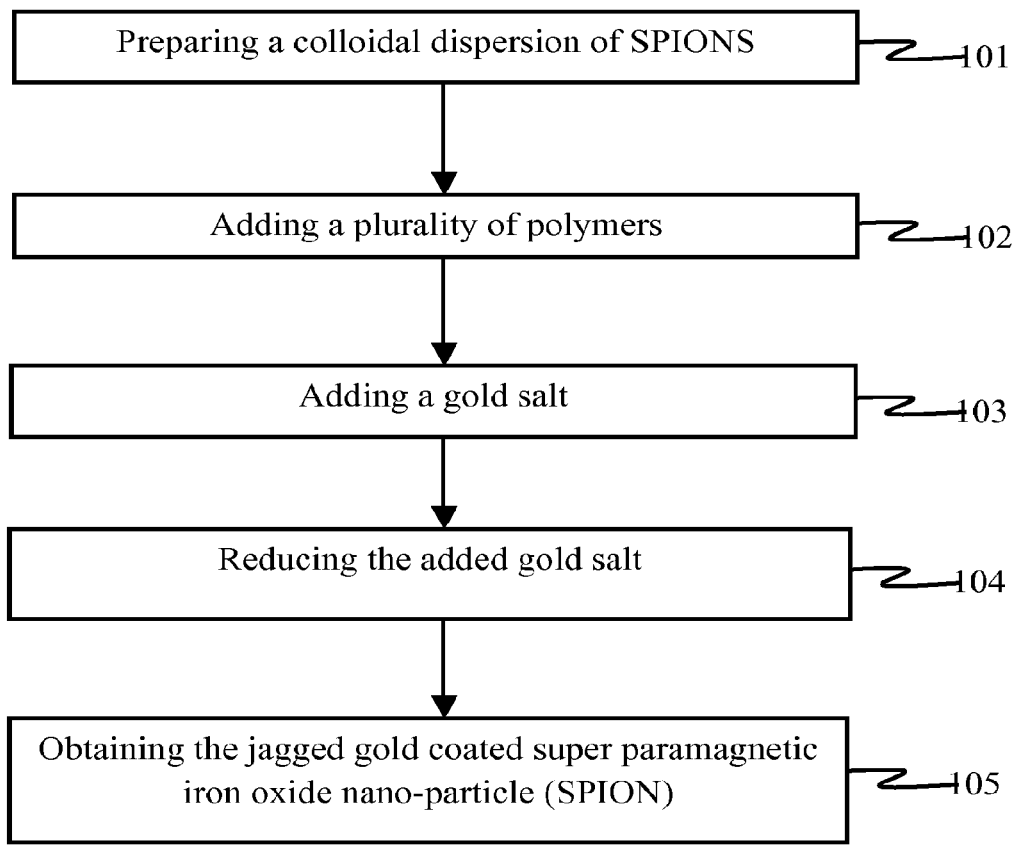
FIG. 1 shows a flow chart explaining the steps of a method of synthesis of gold coated super paramagnetic iron oxide nano-particles (SPIONs), according to one embodiment herein.

FIG. 1 shows a block diagram showing the steps of a method of synthesis of gold coated super paramagnetic iron oxide nano-particles (SPIONs), according to one embodiment herein. With respect to FIG. 1, colloidal dispersion of SPIONS is prepared by a chemical method (101). Plurality of polymers is added (102). A gold salt is added (103). The gold salt is then reduced (104) and the gold coated super paramagnetic iron oxide nano-particle (SPION) are obtained (105). The gold coated super paramagnetic iron oxide nano-particles have jagged surface. The chemical method is selected from a group of methods comprising of a co-precipitation method, a sol-gel method, a micro emulsions method, a hydrothermal method, a thermal decomposition method, a polyol method, a sono chemical method and an electrochemical deposition method. The preferred chemical methods are microemulsions method, thermal decomposition method and polyol method. The plurality of polymers include poly(2-vinyl pyridine), PL-PEG-COOH and Poly-L-histidine. The poly(2-vinyl pyridine) is a pH sensitive polymer. The pH sensitive polymer produces jagged gold coated SPIONS. The PL-PEG-COOH has a stranded shape and the PL-PEG-COOH is a Phospholipid-polyethylene glycol terminated with a carboxylic acid. The poly(2-vinyl pyridine) and Poly-L-histidine act as a template for a gold layer nucleation and growth. The gold salt is Chloroauric acid ($HAuCl_4$) in a concentration of 1%-2%. The gold salt is reduced by a Hydroxylamine Hydrochloride ($NH_2OH.HCl$) solution. The use of pH sensitive polymers controls the formation of jagged shaped gold surfaces. Without the use of pH sensitive polymers, jagged surface of SPIONs is not obtained.

Figure 2:
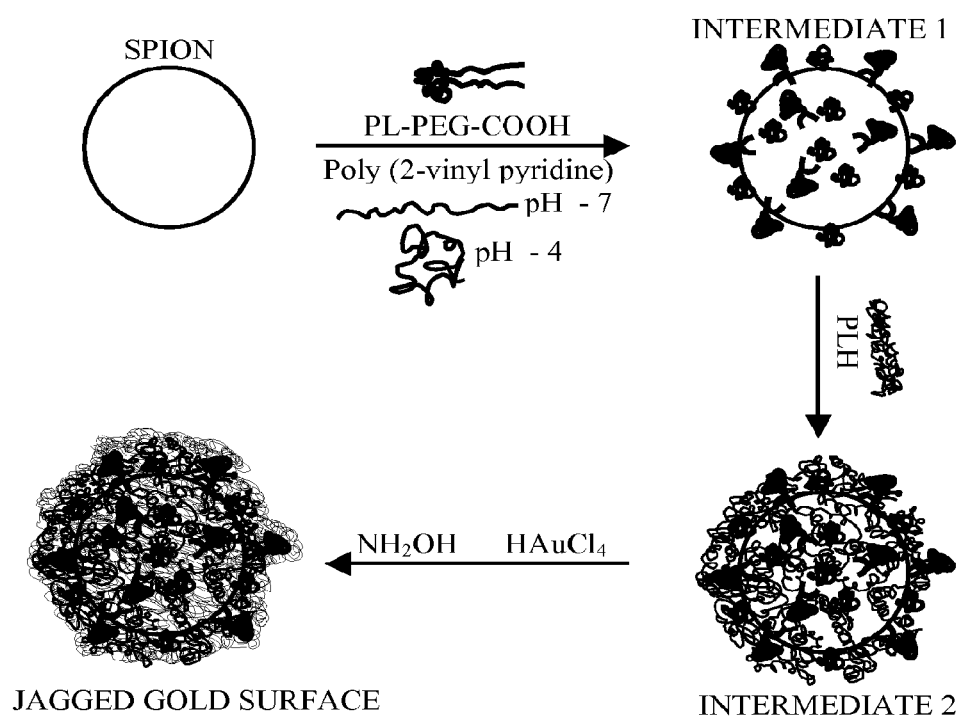
FIG. 2 shows a pictorial representation of the formation of jagged gold surfaced SPIONS, according to an embodiment herein.

FIG. 2 shows a pictorial representation of the formation of jagged and gold surfaced SPIONS, according to an embodiment herein. With respect to FIG. 2, SPION is reacted with poly(2-vinyl pyridine) and PL-PEG-COOH to form an intermediate 1. The polymer molecules of poly(2-vinyl pyridine) and PL-PEG-COOH get deposited on the surface of the SPION. The intermediate 1 is then reacted with poly-L-histidine and forms an intermediate 2. The poly-L-histidine polymer molecules get deposited on the surface of the intermediate 1. This deposition of molecules helps in formation of a gap between the SPION surface and the gold layer. After adding a gold salt i.e. chloroauric acid and reducing with ammonium hydroxide, the jagged gold surfaced SPIONs are obtained. The pH sensitive polymer i.e. Poly(2-vinylpyridine) is employed to create jagged gold surfaces.

Figure 3:
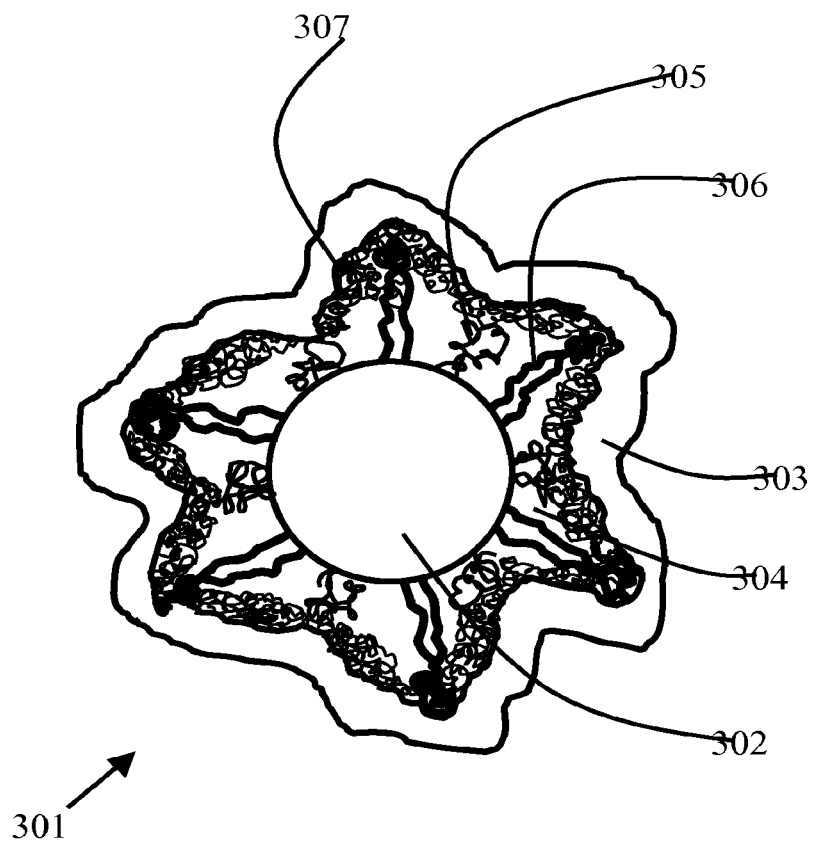
FIG. 3 shows a sectional view of a jagged gold coated SPION, according to an embodiment herein.

FIG. 3 shows a sectional view of a jagged gold coated SPION, according to an embodiment herein. With respect to FIG. 3, core 302 of gold coated SPION 301 is made up of a SPION molecule. Core 302 is covered with a shell 303 made up of a jagged layer or a jagged coating of gold. Polymeric gap 304 exists between core 302 and shell 303. Polymeric gap 304 is made up of pluralities of molecules of different polymers. A unique shape of these polymers helps in creating a gap between core 302 and shell 303. The pluralities of molecules of different polymers include molecules of poly(2-vinyl pyridine) 305, PL-PEG-COOH 306 and Poly-L-histidine 307. Poly(2-vinyl pyridine) 305 is a pH sensitive polymer having a folded shape. PL-PEG-COOH 306 is a Phospholipid-polyethylene glycol terminated with a carboxylic acid having a stranded shape. Poly(2-vinyl pyridine) 305 and Poly-L-histidine 307 act as a template for a growth and nucleation of the jagged gold layer. The unique shapes of these polymeric molecules provide the so called jagged surface to the gold coating.

Figure 4:
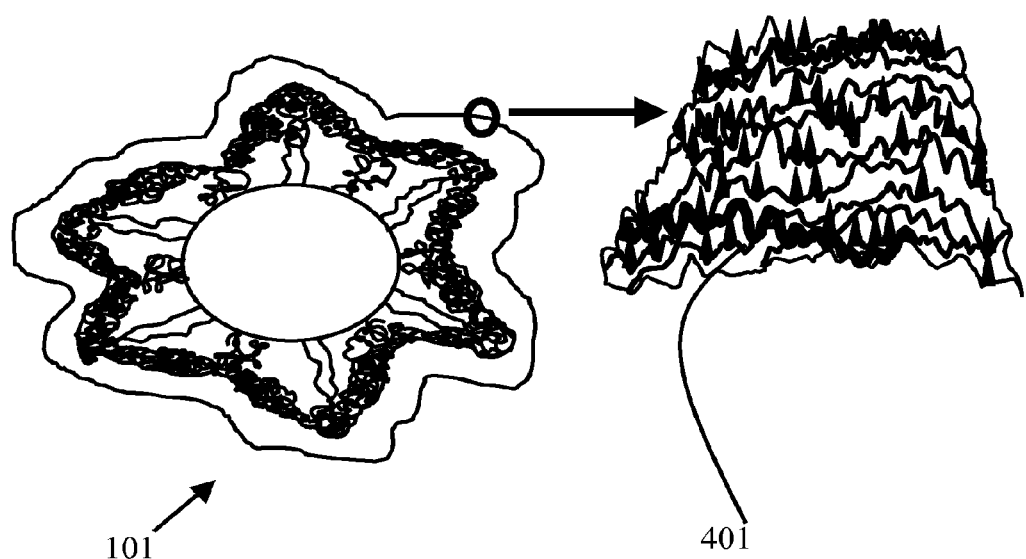
FIG. 4 shows an enlarged view of a gold shell of a jagged gold coated SPION, according to an embodiment herein.

FIG. 4 shows an enlarged view of a gold shell of a jagged gold coated SPION, according to an embodiment herein. With respect to FIG. 4, an enlarged view of shell 303 of gold coated SPION 301 can be seen. The figure shows the achieved jagged surface 401 of shell 303 on the surface of SPION core 302.

Experimental Data

Materials $FeCl_2.4H_2O$, $FeCl_3.6H_2O$, diethylene glycol, sodium hydroxide (NaOH), NH2 OH.HCL, gold salt ($HAuCl_4$) Poly-L-histidine (PLH), and Poly (2-vinylpyridine) were purchased from Sigma-Aldrich. It is noteworthy that PLH and Poly(2-vinylpyridine) were used as the templates to direct gold. nucleation and growth. Phospholipid-polyethylene glycol terminated with carboxylic acid (PL-PEG-COOH) was purchased from Avanti polar lipids. Pyridine was obtained from Sinophami Chemical Reagent Company.

Synthesis of SPIONs

In order to obtain nanoparticles with a narrow size distribution, the polyol route was employed. Briefly, 5 mL of an aqueous solution of $FeCl_2.4H_2O$ (0.045 mol) and $FeCl_3$ (0.0375 mol) were added to 250 mL of diethyleneglycol. The mixture was heated to 170° C. and maintained at this temperature for 15 min before addition of the base (i.e. solid NaOH (0.375 mol)). Afterward, the temperature was maintained at 170° C. for a period of 1 h before cooling at 60° C. The synthesized SPIONs were collected with neodymium magnet and washed with 100 mL of a $HNO_3$ 1N solution.

Formation of Smooth Gold-Shell on the Surface of SPIONs

The smooth gold-shell SPIONs were prepared. Briefly, the prepared SPIONs were mixed with PL-PEG-COOH (ratio of 1:1.5 W/W) in chloroform, and remained till the solvent were evaporated slowly. The residual coated SPIONs were heated to 80° C. for 5 min and redispersed in DI water with sonication. The obtained materials were collected with strong magnet and washed several times with DI water. PLH was added to the solution of SPIONs and the pH was adjusted among 5-6, using 0.1 N HCl. After incubation for 60 min, the magnetic NPs were collected with magnet and washed several times with DI water. The obtained solution was mixed with $HAuCl_4$ (w/w 1%), for 20 min where the pH was adjusted among 9-10 with NaOH. Afterward, $NH_2OH.HCL$ was added to the solution and mixed well till the colour of colloidal suspension turned to dark blue. It is noteworthy that the observed colour was cleared in a few minutes. The achieved solution was washed several times, redispersed in DI water using sonicator, and kept between 2-8° C.

Formation of Jagged Gold-Shell on the Surface of SPIONs

In order to create the jagged-shaped gold-coated SPIONs, the prepared SPIONs were mixed with Poly(2-vinylpyridine) and PL-PEG-COOH (ratio of 1:1.5 (the same concentration of polymers were employed) W/W) and the same other stages of preparation of smooth gold shell were followed except the final section (i.e. addition and reduction of gold salts). More specifically, the solution containing Poly (2-vinylpyridine) and PL-PEG-COOH coated SPIONs, after PLH addition, was mixed with $HAuCl_4$ (w/w 1%), for 20 min where the pH was adjusted among 4-5 with NaOH. In this pH, Poly(2-vinylpyridine), which is the pH sensitive polymer, has folded formation where PL-PEG-COOH has stranded shape. It is noteworthy to mention that using pH sensitive polymer was vital for the formation of jagged surfaces; in this case, Poly(2-vinylpyridine) has folded shape in comparison with PL-PEG-COOH, which is branded. After reduction of gold with NH2 OH.HCL, the jagged gold coated SPIONs was obtained. The achieved solution was washed several times, redispersed in DI water using sonicator, and kept between 2-8° C.

Measurements and Instrumentation

Dynamic light scattering (DLS) and zeta potential methods were used to measure the average diameters and surface zeta potential of various synthesized SPIONs. Dynamic light scattering measurements were performed with a Malvern PCS- 4700 instrument equipped with a 256-channel correlator. The 488.0 nm line of a Coherent Innova-70 Ar ion laser was used as the incident beam. The laser power used was 250 mW. The scattering angles, θ, employed ranged between 40°-140°. The temperature was maintained at 25° C. with an external circulator. Zeta potential determination was performed using a Malvern Zetasizer 3000 HSa. Each measurement was an average of six repetitions of one minute each and repeated five times. Data analysis has been performed according to standard procedures, and interpreted through a cumulant expansion of the field autocorrelation function to the second order. Moreover, in order to obtain a distribution of decay rates, a constrained regularization method, CONTIN, was used to invert the experimental data.

Figure 5A:
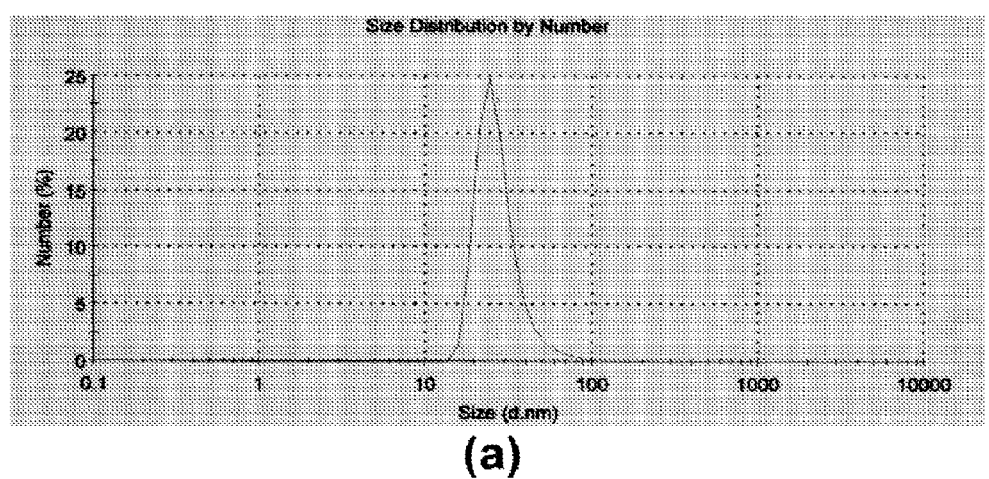
FIG. 5A shows a Dynamic Light Scattering (DLS) graph of a smooth gold coated SPION.

FIG. 5A shows a Dynamic Light Scattering (DLS) graph of a smooth gold coated SPION. With respect to FIG. 5A, the formation of nano-particles with a very narrow size distribution was observed.

Figure 5B:
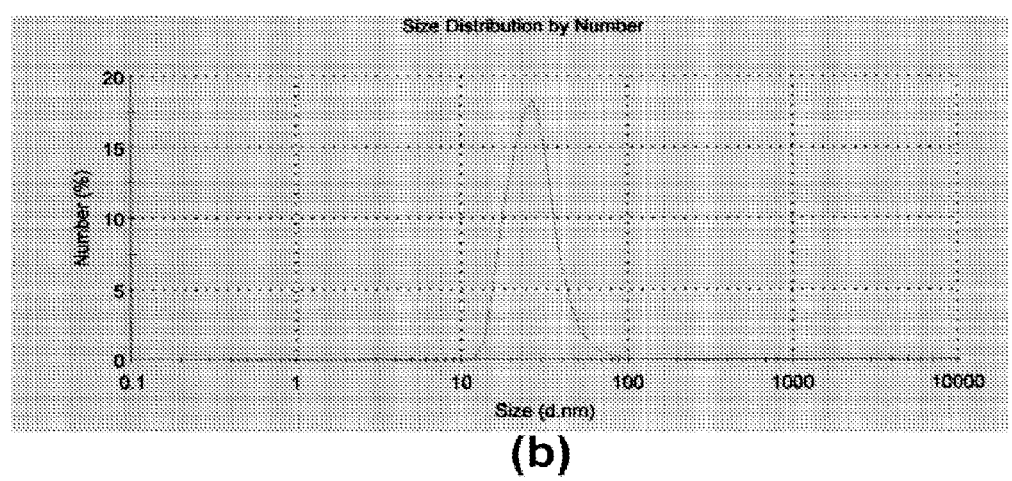
FIG. 5B shows a DLS graph of a jagged-shaped gold coated SPION, according to an embodiment herein.

FIG. 5B shows a DLS graph of a jagged-shaped gold coated SPION, according to an embodiment herein. With respect to FIG. 5B, the formation of nano-particles with a very narrow size distribution was observed.

Figure 5C:
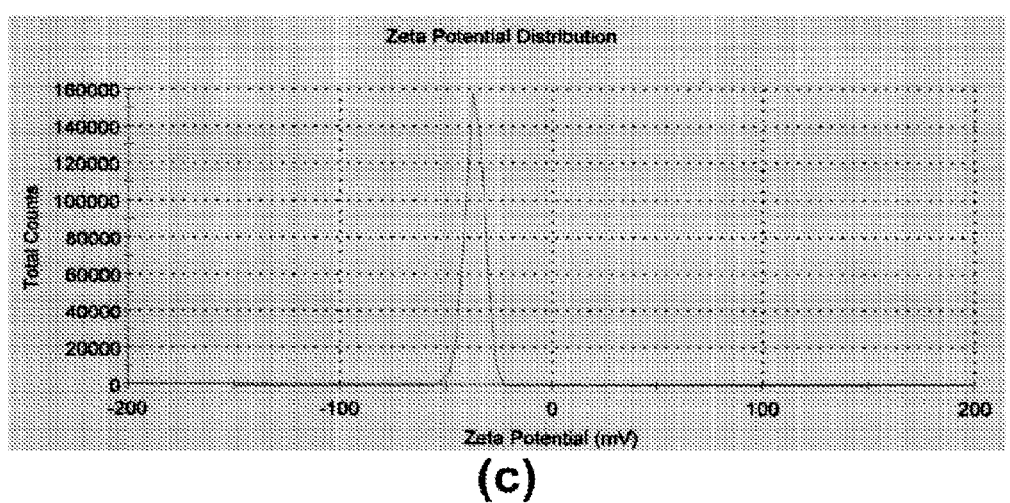
FIG. 5C shows a zeta potential curve of a smooth gold coated SPION.

FIG. 5C shows a zeta potential diagram of a smooth gold coated SPION. With respect to FIG. 5C, a single peak was observed due to a smooth surface of the gold coated SPIONs.

Figure 5D:
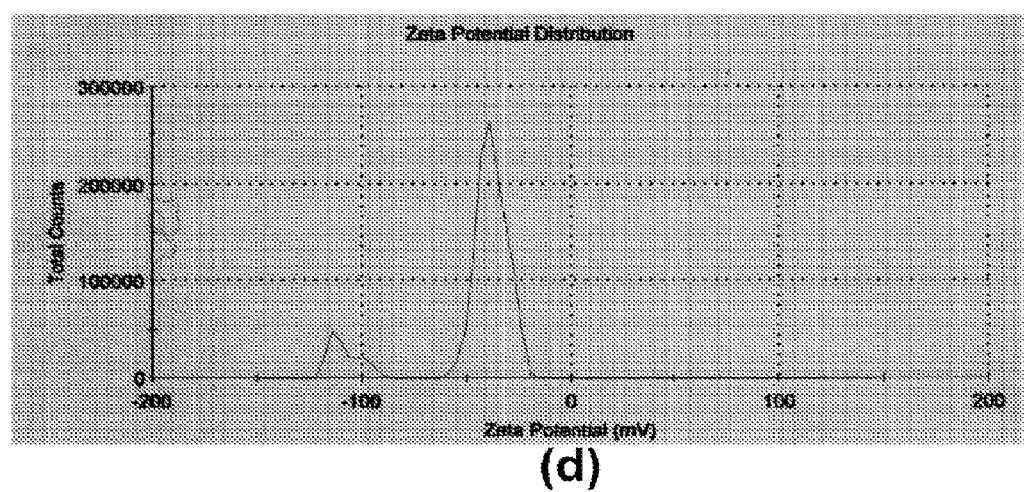
FIG. 5D shows a zeta potential curve of a jagged-shaped gold coated SPION, according to an embodiment herein.

FIG. 5D shows a zeta potential diagram of a jagged-shaped gold coated SPION, according to an embodiment herein. FIG. 5D shows two peaks due to the existence of keen edges in jagged gold coated SPIONs.

The results obtained by DLS and zeta potential methods are shows in Table 1. Table 1 shows the observed values of several parameters of the prepared SPIONs. Table 1 summarizes the very narrow size distribution of prepared SPIONs.

Table 1 shows a SPIONs size distribution obtained by Dynamic Light Scattering and Zeta Potential determination methods by a particulate micro-electrophoresis of the differently coated SPIONs.

| Nano-particles | $D_H(nm)^a$ | $PDI^b$ | $<D_H>(nm)^c$ | Zeta potential (mV) |
|---|---|---|---|---|
| Bare | 13.7 ± 2.1 | 0.29 | 18.3 ± 3.2 | +43.7 ± 1.7 |
| Smooth gold coated SPIONs | 27.8 ± 2.6 | 0.19 | 34.2 ± 2.2 | −36.5 ± 1.56 |
| Jagged gold coated SPIONs | 28.1 ± 2.8 | 0.17 | 7.4 ± 2.7 | −37.6 ± 1.29 −108 ± 3.54 |

$^a$z-average hydrodynamic diameter extracted by cumulant analysis of the data.
$^b$Polydispersity Index.
$^c$Average hydrodynamic diameter determined from CONTIN size distribution. Sizes are presented as mean ± SD of four samples.

With respect to table 1, the zeta potential of the jagged-shaped gold-coated SPIONs displayed two individual populations. This happened due to the significant differences between the gradient of the counter ions in keen edge of the jagged surface and smooth sections.

Morphologies and shape of the prepared SPIONs were probed by Transmission Electron Microscopy (TEM) and Atomic Force Microscopy (AFM). The size and shape of the SPIONs were evaluated with a Phillips CM200 transmission electron microscope equipped with an AMT 2×2 CCD camera at an accelerating voltage of 200 kV. To prepare samples for TEM, a drop of the suspension was placed on a copper grid and dried.

Figure 6A:
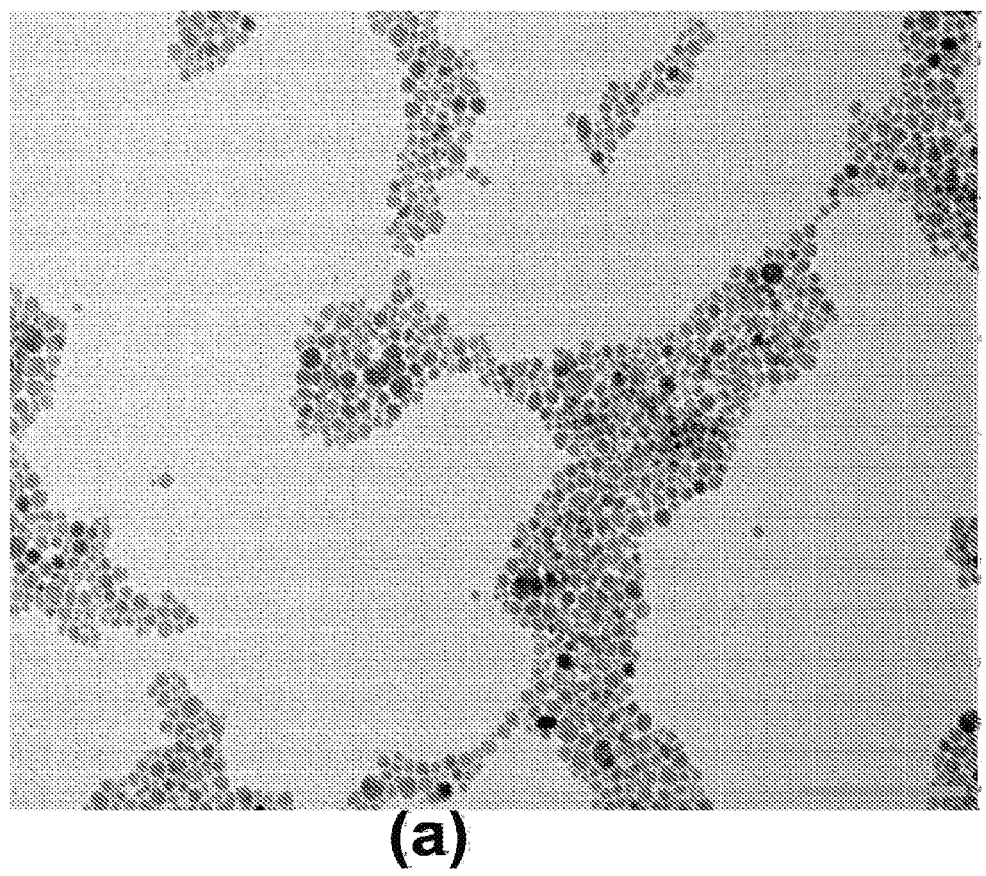
FIG. 6A shows Transmission Electron Microscopic (TEM) image of bare SPIONs.

FIG. 6A shows Transmission Electron Microscopic (TEM) image of bare SPIONs. With respect to FIG. 6A, a formation of magnetic nano-particles with very narrow size distribution is observed. The scale bare is 100 nm.

Figure 6B:
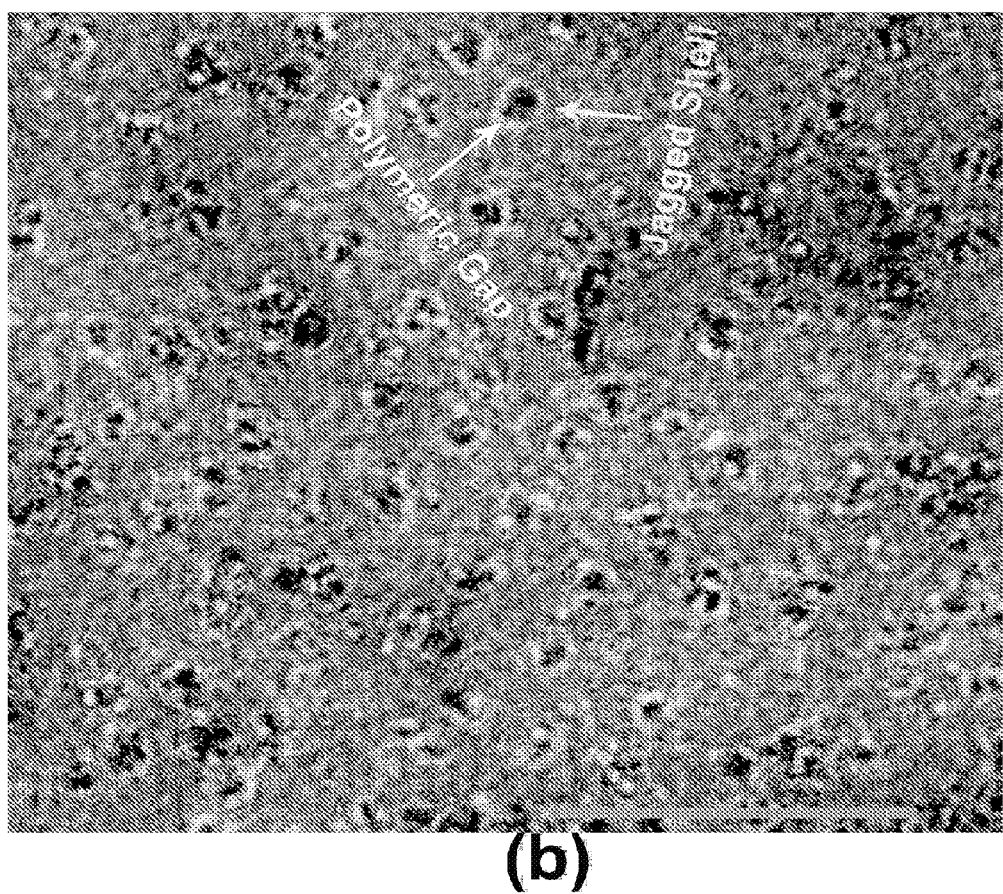
FIG. 6B shows a TEM image of jagged-shaped gold coated SPIONs, according to an embodiment herein.

FIG. 6B shows a TEM image of jagged-shaped gold coated SPIONs, according to an embodiment herein. With respect to FIG. 6B, an existence of the polymeric gap between the SPION core and gold ring together with the existence of rough surface morphology was observed. The scale bare is 100 nm.

High-resolution surface imaging studies were performed using Atomic Force Microscopy (AFM) to estimate surface morphology and particle size distribution. The samples were imaged with the aid of Dualscope/Rasterscope C26, DME, Denmark, using DS 95-50-E scanner with vertical z-axis resolution of 0.1 nm.

Figure 7A:
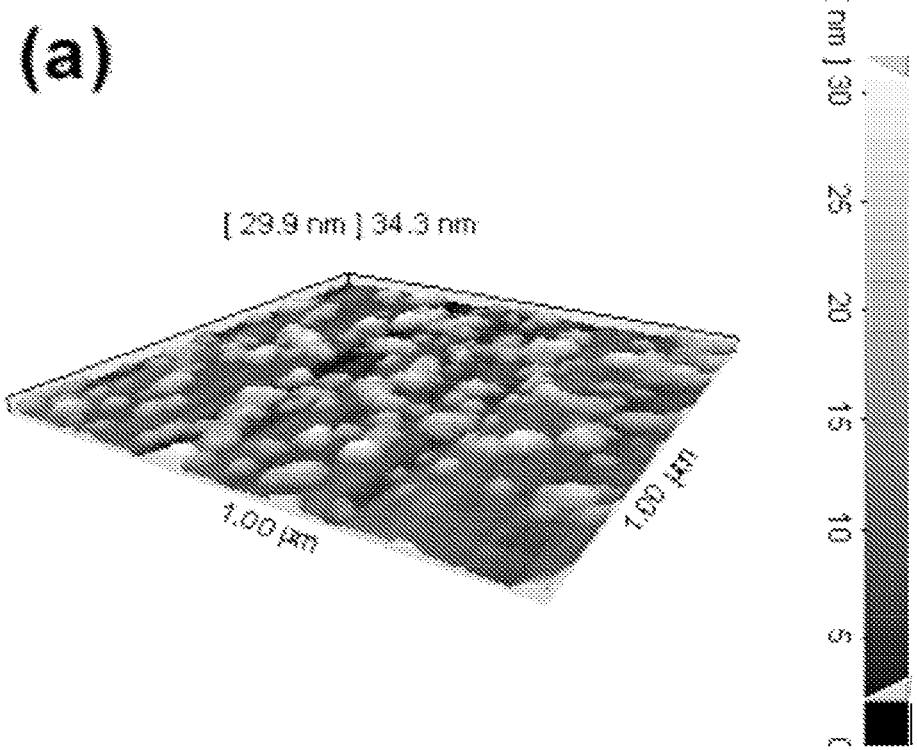
FIG. 7A shows an Atomic Force Microscopic (AFM) image of a smooth gold coated SPION.

FIG. 7A shows an Atomic Force Microscopic (AFM) image of a smooth gold coated SPION. With respect to FIG. 7A, the maximum size of the smooth gold coated SPIONs was estimated approximately 20-30 nm.

Figure 7B:
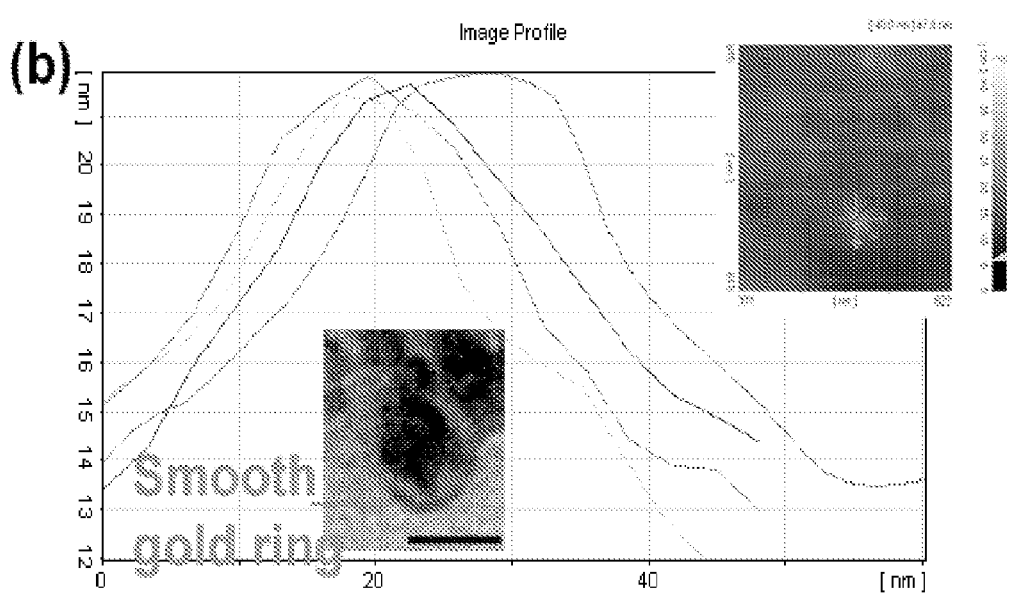
FIG. 7B shows an image profile according to the obtained AFM image of smooth gold coated SPION.

FIG. 7B shows an image profile according to the obtained AFM image of smooth gold coated SPION. With respect to FIG. 7B, the formation of smooth gold coated SPION can be seen in various axes. The average particle diameter of the smooth gold coated SPION was estimated approximately 15-25 nm. The image profile displayed the surface smoothness of the smooth gold coated SPION.

Figure 7C:
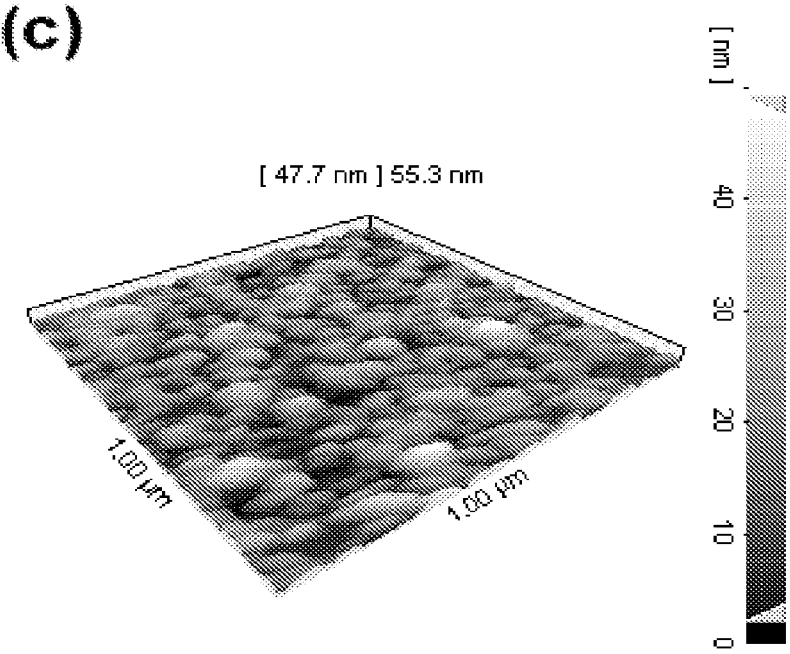
FIG. 7C shows an AFM image of a jagged-shaped gold coated SPION, according to an embodiment herein.

FIG. 7C shows an AFM image of a jagged-shaped gold coated SPION, according to an embodiment herein. With respect to FIG. 7C, the average particle was estimated approximately 30-40 nm.

Figure 7D:
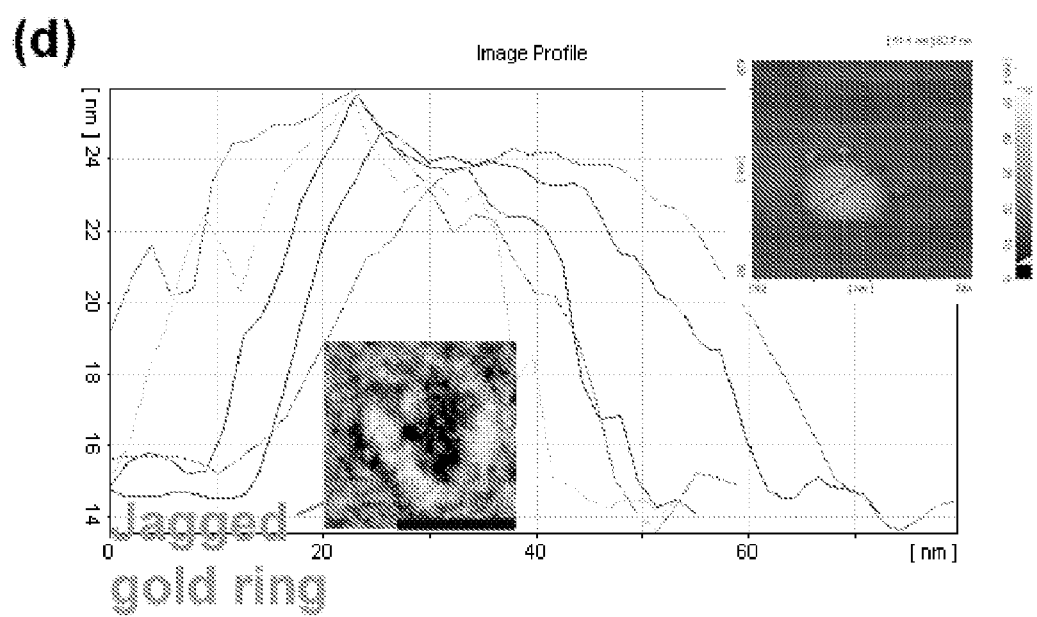
FIG. 7D shows an image profile according to the obtained AFM image of the jagged-shaped gold coated SPION, according to an embodiment herein.

FIG. 7D shows an image profile according to the obtained AFM image of the jagged-shaped gold coated SPION, according to an embodiment herein. With respect to FIG. 7D, the formation of jagged gold coated SPION can be seen in various axes. The average particle size distribution of the gold coated SPIONs varied between 0-50 nm. The TEM results together with AFM results illustrate a very jagged gold ring shell on the surface of SPIONs with a polymeric gap.

SERS Activity of Smooth and Jagged Gold Coated SPIONS

Due to the existence of the gold shell on the surface of SPIONs, the coated SPIONs have considered as an SERS active nano-particles and in order to check their SERS activity. Raman spectra were achieved by employing of a confocal microprobe Raman system (HR800, Jobin Yvon), which is a single spectrograph instrument equipped with a holographic notch filter and a CCD detector. The size of the slit and pinhole were 100 and 400 μm, respectively. A long working distance 50× objective was used to collect the Raman scattering signal. The excitation wavelength was 632.8 nm from a He—Ne laser, and the greatest laser power was 10 mW. The smooth and jagged gold coated SPIONs were collected in a vial by a strong magnet that is placed at the center on the bottom side of the vial, respectively. The SERS activities of the collected nanoparticles were measured in situ, using the confocal microprobe Raman system.

Figure 8:
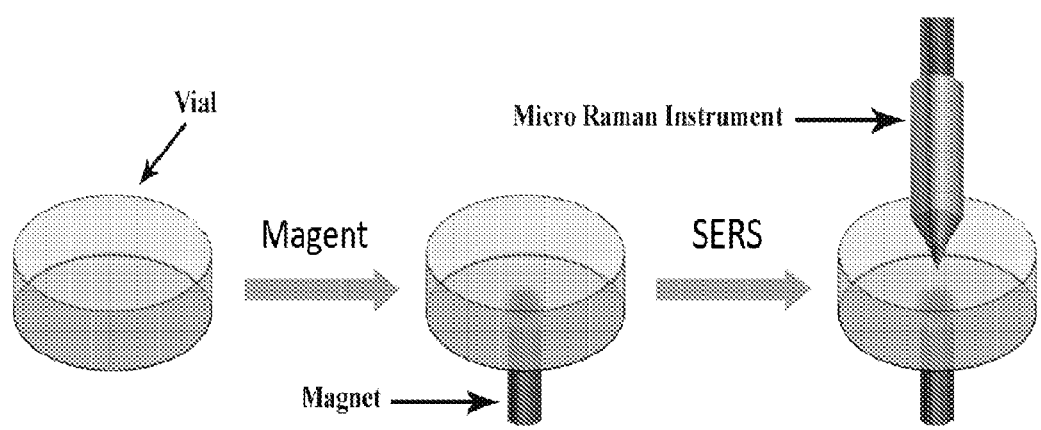
FIG. 8 shows a block diagram showing the steps of method of performing Surface Enhanced Raman Spectroscopy (SERS) of jagged gold coated SPIONs, according to one embodiment herein.

FIG. 8 shows a block diagram showing the steps of method of performing Surface Enhanced Raman Spectroscopy (SERS) of jagged gold coated SPIONs, according to one embodiment herein. With respect to FIG. 8, the jagged gold coated SPIONs were collected in a vial by strong magnet by placing the magnet at the center of the vial. The SERS activities of the collected nanoparticles were measured in situ, using the confocal microprobe Raman system. The detection of SERS for the jagged coated SPIONs was conducted by absorption of pyridine on the surface of magnetic nano-particle to prove the important effects of jagged-shaped gold coated SPIONs.

Figure 9:
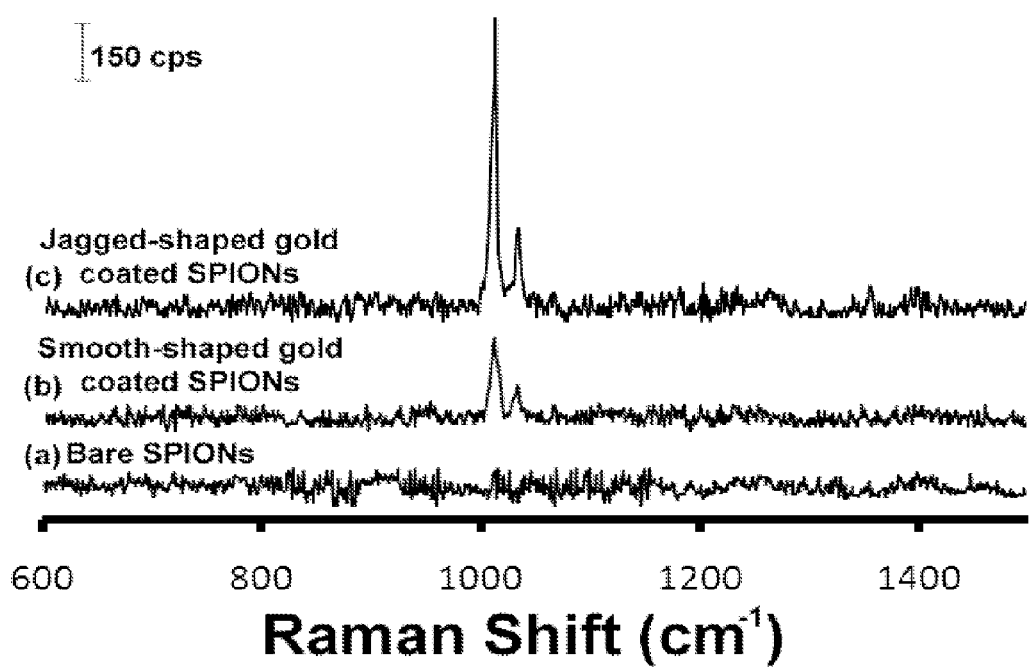
FIG. 9 shows a SERS spectrum of absorbed pyridine by the nano-particles, where (a) shows SERS spectrum for bare SPIONs, where (b) shows a SERS spectrum of smooth gold coated SPIONs and where (c) shows a SERS spectrum of jagged-shaped gold coated SPIONs, according to an embodiment herein.

FIG. 9 shows a SERS spectrum of absorbed pyridine by the nano-particles, where (a) shows SERS spectrum for bare SPIONs, where (b) shows a SERS spectrum of smooth gold coated SPIONs and where (c) shows a SERS spectrum of jagged-shaped gold coated SPIONs, according to an embodiment herein. Pyridine was used as model molecule for SERS because pyridine has a well-documented Raman spectral data and a large Raman scattering cross section. In order to check the capability of nanoprobes to track the pyridine interaction, 10 µM of pyridine was added to the nano-particles' solution and incubated for 20 min. With respect to FIG. 9, it is clear that the SERS spectra of bare SPIONs did not show any characteristic peak of pyridine whereas the gold coated SPIONs with jagged shape displays significantly higher SERS signal intensity in comparison with the smooth one. The peak around 1000 $cm^{-1}$ that corresponds to ring breathing vibration modes of Pyridine adsorbed on gold surfaces.

The enhanced Raman peak intensity of the jagged gold surfaces is not only due to the higher absorbance of the pyridine on the jagged surfaces, in comparison with the smooth one, but also due to existence of the keen edge on the surface of jagged gold.

The embodiments herein present a new class of SPIONs-gold core-shell nano-particles. In contrast to previous arts in which gold shells are deposited directly on SPIONs, the core and shell of our particles are spatially separated with a dielectric polymer layer. Using stimuli sensitive polymers, the gold shell were deposited in the jagged shape on the surface of SPIONs, with non-uniform polymeric gap. The obtained magnetic nano-particles show surface enhance Raman spectroscopy in addition to the other reported properties including electronic, magnetic, optical, acoustic and thermal responses, which allow multimodality imaging. We visualized that the prepared jagged gold surface also allows simple conjugation with various type of biomolecular through thiol binding that enhances an all-in-one nanoprobe for non-invasive imaging and molecular theranosis of complex diseases.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. A gold coated super paramagnetic Iron oxide nano-particle (SPION) comprising;
    a core, and wherein the core includes a super paramagnetic Iron oxide nano-particle;
    a shell, and wherein the shell includes a jagged coating of gold; and
    a gap between the core and the shell, and wherein the gap is a polymeric gap, and wherein the gap is a non uniform gap, and wherein the gap includes a plurality of polymeric molecules, and wherein the plurality of polymeric molecules includes poly (2-vinyl pyridine), PL-PEG-COOH and Poly-L-histidine, and wherein the poly (2-vinyl pyridine) is a pH sensitive polymer, and wherein the poly (2-vinyl pyridine) controls a formation of jagged shaped gold surfaces,
    wherein poly (2-vinyl pyridine) has folded shape, and wherein PL-PEG-COOH has a stranded shape,
    wherein the gold coated SPIONS with a jagged surface conjugates with bio molecules to provide a nano probe for molecular diagnosis and cellular tracking, medical imaging and therapeutic applications, and molecular theragnosis, wherein therapeutic applications include a drug delivery and a simultaneous drug delivery and imaging application properties.

2. The gold coated SPION according to claim 1, wherein the core is made up of a magnetite.

3. The gold coated SPION according to claim 1, wherein the PL-PEG-COOH is a Phospholipid-polyethylene glycol terminated with a carboxylic acid.

4. The gold coated SPION according to claim 1, wherein the poly (2-vinyl pyridine) and the Poly-L-histidine act as a template for a growth and nucleation of the jagged gold coating.

5. A method of synthesizing a gold coated super paramagnetic iron oxide nano-particle (SPION) comprising steps of:
    preparing a colloidal dispersion of SPIONS, wherein the colloidal dispersion of SPIONS is prepared by a chemical process;
    adding a plurality of polymers to form a mixture, wherein the plurality of polymers include a poly (2-vinyl pyridine) polymer and a PL-PEG-COOH polymer;
    heating the mixture to 80° C. for 5 mins;
    dispersing the heated mixture in DI water with sonication;
    adding a polymer to the dispersed and sonicated mixture to form an another mixture, wherein the polymer is a Poly-L-histidne polymer;
    adding a gold salt to the another mixture and mixing the another mixture with the added gold salt for 20 mins;
    adjusting a pH of the mixed another mixture with the added gold salt to 4-5, wherein the pH is adjusted using a NaOH solution;
    reducing the added gold salt; and
    acquiring the gold coated super paramagnetic iron oxide nano-particle (SPION) in a form of a solution, wherein the gold coating is jagged; and
    keeping the formed solution between 2-8° C. by re-dispersing in a deionized water using a sonicator.

6. The method according to claim 5, wherein the chemical process is selected from a group of processes comprising of a co-precipitation method, a sol-gel method, a microemulsions method, a hydrothermal method, a thermal decomposition method, a polyol method, a sonochemical method and an electrochemical deposition method, wherein the chemical method is a microemulsions method, a thermal decomposition method and a polyol method.

7. The method according to claim 5, wherein the poly (2-vinyl pyridine) polymer is a pH sensitive polymer.

8. The method according to claim 7, wherein the pH sensitive polymer produces jagged gold coated SPION's.

9. The method according to claim 5, wherein the PL-PEG-COOH polymer has a stranded shape and wherein the PL- PEG-COOH polymer is a Phospholipid-polyethylene glycol polymer terminated with a carboxylic acid.

10. The method according to claim 5, wherein the poly (2-vinyl pyridine) polymer and the Poly-L-histidine polymer act as a template for a growth and nucleation of the jagged gold coating.

11. The method according to claim 5, wherein the gold salt is Chloroauric acid ($HAuCl_4$) and wherein a concentration of the gold salt is 1%-2%.

12. The method according to claim 5, wherein the gold salt is reduced by a Hydroxylamine Hydrochloride ($NH_2OH.HCl$) solution.

13. The method according to claim 5, wherein a ratio of SPIONS:Poly (2-vinylpyridine) is 1:0.6-0.9 w/w, wherein a ratio of SPIONS:PL-PEG-COOH is 1:0.6-0.9 w/w, wherein a ratio of spions:PLH is 1:1-2 w/w, and wherein a ratio of spions:HAuCl4 is 1: 1-2%.

14. The gold coated SPION according to claim 1, wherein the gold coated SPION has an average particle size of 15 nm.

* * * * *